United States Patent [19]

Spira-Solomon et al.

[11] Patent Number: 5,229,301
[45] Date of Patent: Jul. 20, 1993

[54] MASS BIOSENSOR METHOD WITH QUANTIFIED SENSOR RENEWAL

[75] Inventors: Darlene J. Spira-Solomon, Stanford; May Tom-Moy, San Carlos; Carl A. Myerholtz, Cupertino, all of Calif.

[73] Assignee: Hewlett-Packard Company, Palo Alto, Calif.

[21] Appl. No.: 711,786

[22] Filed: Jun. 7, 1991

[51] Int. Cl.$^5$ ................. G01N 33/543; G01N 33/551
[52] U.S. Cl. ................. 436/518; 436/501; 436/527; 436/800; 436/805
[58] Field of Search ............... 436/501, 518, 527, 800, 436/805

[56] References Cited

U.S. PATENT DOCUMENTS

| | | | |
|---|---|---|---|
| 4,666,866 | 5/1987 | Krauth | 436/518 |
| 4,800,166 | 1/1989 | Horn et al. | 436/89 X |
| 4,937,200 | 6/1990 | Kumazawa et al. | 436/518 |

OTHER PUBLICATIONS

Eleftherios P. Diamandis, "Immunoassays with Time-Resolved Fluorescence Spectroscopy: Principles and Applications", *Clinical Biochemistry*, vol. 21, Jun. 1988, pp. 139-150.
Eleftherios P. Diamandis and Theordore K. Christopoulos, "Europium Chelate Labels in Time-Resolved Fluorescence Immunoassays and DNA Hybridization Assays", *Analytical Chemistry*, vol. 62, No. 22, Nov. 15, 1990, pp. 1149-1157.
Ramon A. Evangelista et al., "A New Europium Chelate for Protein Labelling and Time-Resolved Fluorometric Applications", *Clinical Biochemistry*, vol. 21. Jun. 1988, pp. 173-178.

*Primary Examiner*—Esther L. Kepplinger
*Assistant Examiner*—Lora M. Green

[57] ABSTRACT

A mass biosensor method provides enhanced quantification of analyte concentrations in a sample. In a direct approach, an analyte is derivatized to form an analyte chelate and then specifically bound to a sensor. In an indirect approach, a complement of the analyte is derivatized to form a complement chelate which is then bound to a sensor. In a direct/indirect hybrid approach, an analog of the analyte is derivatized to form an analog chelate that is bound to a sensor in competition with the sample analyte. In all three approaches, mass measurements taken as the ligand chelate attaches to the sensor permit the concentration of the analyte in the sample to be calculated. Once measurement is completed, a dissociation treatment is applied to dissociate the derivatized species from the sensor so that the sensor can be reused. The effects of the dissociation treatment can be monitored using phosphorescence detection. The results obtained during monitoring can be compared with a predetermined threshold to ensure complete dissociation while avoiding alteration of the sensor surface. This procedure permits precision renewal of a sensor to maximize the number of times a sensor can be used. Moreover, this method allows quantification to be performed using the same sensor and coating in place during calibration, minimizing systematic errors and enhancing quantification accuracy.

12 Claims, 6 Drawing Sheets

MASS BIOSENSOR METHOD WITH QUANTIFIED SENSOR RENEWAL

BACKGROUND OF THE INVENTION

The present invention relates to analytical chemistry and, more particularly, to analyte quantification using a mass biosensor system. A major objective of the present invention is to provide for more accurate biosensor quantifications.

Mass biosensor systems use sensors with a biochemical coating that selectively binds a sample component to the substantial exclusion of other sample components. Monitoring mass change that occurs due to the binding permits quantification of even trace amounts of an analyte, i.e., a component of interest, in a sample. Biosensor applications include protein analysis, blood/urine analysis, and environmental studies requiring that the amounts of various pollutants on land and in water be monitored.

There are contrasting strategies for quantifying a sample analyte using a mass biosensor. In a "direct" strategy, a sensor is coated with a "complement" of the sample analyte. Herein, a "complement" of a chemical selectively binds that chemical. For example, to directly quantify an antigen analyte, a sensor is coated with the complementary antibody. When the sample is introduced to the sensor, sample antigen analyte is bound to the antibody, and thus to the sensor. The initial rate at which analyte binds is directly related to the concentration of the sample analyte. Thus, monitoring the rate of mass change due to this binding permits the sample analyte concentration to be determined.

In an "indirect" approach, the sample analyte is not bound to the sensor. The sensor is prepared with a coating which is an analog of the analyte. An "analog" of an analyte is a chemical entity that behaves the same with respect to a given complement to the analyte as does the analyte itself. An analyte is necessarily an analog of itself, and derivatives of an analyte can be analogs. A prequantified complement to the analyte is added to the sample, which is then introduced to the sensor. The sample analyte competes with the analog coating on the sensor for the complement; thus, a higher analyte concentration corresponds to a slower rate of binding to the sensor. The mass of the complement binding to the sensor is monitored, permitting the concentration of the analyte in the sample to be determined.

To provide a description of mass biosensor operation that is applicable to both the direct and indirect strategies, the term "binder" refers to the selective sensor coating, and the term "ligand" is used to refer to the substance that the selective sensor coating specifically binds. In the direct strategy, the ligand is the analyte and the binder is the complement of the ligand. In the indirect strategy, the ligand is the complement of the analyte, and the binder is the analog of the analyte. The binding between the ligand and binder is "specific" in that it occurs between respective specific molecular locations on the ligand and binder. Mechanisms for specific binding can include electrostatic binding, hydrogen bonds, and van der Waals (hydrophobic) binding.

One type of mass biosensor uses a piezoelectric crystal as an acoustic waveguide. An input transducer generates a periodic acoustic signal from a periodic electrical input signal. The acoustic signal propagates through the crystal to an output transducer that converts the received acoustic signal to an electrical output signal. The propagation velocity of the acoustic signal changes as the mass of ligand bound to the surface of the crystal changes.

In one sensor system configuration, a "sample" signal passes through a "sample" sensor, and an identically generated "reference" signal is passed through a "reference" sensor. The reference and sample sensors are matched, except for the affinities of the coatings. While the sample sensor coating has an affinity for the ligand of interest, the reference coating does not specifically bind that ligand. Preferably, the reference coating is selected to match the molecular mass and other binder properties, with the exception of ligand affinity.

When sample is introduced to the sample sensor, ligand binds to the binder, increasing the mass attached to the sensor, and thus, the propagation velocity of the sample signal changes. The change in propagation velocity is reflected in a change of phase in the sample signal. The phase changes can be monitored by comparing the sample signal phase with that of the reference signal. Initially, the sample signal phase increases in proportion to the concentration of the ligand in the sample, exclusive in the indirect approach of ligand bound to analyte. As binding sites become occupied, the binding rate decreases. If sufficient time is provided for an equilibrium to be reached between binding and dissociation, the net binding rate falls to zero; the mass at equilibrium can be used to calculate the analyte concentration. However, the initial mass change rate, as indicated by the initial phase change rate, provides for the determination of analyte concentration before and whether or not equilibrium is achieved.

As is apparent from the foregoing, there is no requirement that mass be determined explicitly for concentration to be determined. Accordingly, "mass measurement" and "monitoring mass" encompass detecting and monitoring variables that vary with mass. As explained above, the primary variable used to determine analyte concentration is the initial phase change rate provided by a mass biosensor system when a sample is introduced to the incorporated sample sensor. Alternative variables are equilibrium phase offset, frequency, explicitly determined mass or mass change rate, and other mass-sensitive variables associated with other types of mass biosensor systems.

The algorithm used to calculate analyte concentration in a sample depends on the measurement strategy employed. In the direct approach, the analyte is bound to the sensor so that analyte concentration is directly related to the initial phase change rate and the affinity binding constant for ligand analyte and the binder sensor coating. In the indirect approach, the ligand is the complement and its concentration is predetermined. The sample analyte and the analog binder compete for the predetermined quantity of ligand. A greater quantity of analyte more effectively competes for the ligand complement, and results in a lower initial phase change rate. The algorithm used in the indirect approach reflects this competition. In either approach, the appropriate algorithm preferably involves comparing measurement results with one or more calibration points determined from "standard" calibration measurements using known quantities of analyte.

The accuracy of a biosensor measurement is limited by the repeatability of the measurement process. Ideally, two measurements of the same sample yield the same measurements, and the differences between measurements reflect the differences between samples to the exclusion of artifacts. To the extent that ambient conditions and sensor variations contribute to measurement differences, measurement accuracy is impaired. This impairment applies generally to comparisons between measurements, and, more specifically, between a sample measurement and one or more blank measurements used to calibrate measurements. A lower repeatability impairs the validity of the calibration, and, thus, the accuracy of the measurement.

The repeatability of a biosensor method is affected by the nature of the bond attaching the binder to the substrate. Binder can be covalently attached or nonspecifically adsorbed to an underlying substrate, either directly or through an intermediate structure. Adsorption results in relatively weak attachment of binder molecules in random, unknown, and/or unstable orientations. Weakly attached binder can become dissociated during or between measurements, impairing repeatability. Some orientations can prevent ligands from reaching a binding site on a binder molecule. Finally, the relative instability of adsorbed binder can subject the binder to indeterminate effects due to the action of sample components, some of which may be unknown or uncharacterized. All of these disadvantages limit the repeatability of measurements using these sensors and subject measurements to systematic distortions due to differences in the coatings between the time of calibration and the time of measurement.

More recently, techniques have been developed for covalently binding a wide variety of ligand binders to the substrate of a sensor of a mass biosensor system. Covalent bonds are relatively stable and provide the binder with a predictable orientation that can ensure the accessibility of the binding sites required for ligand binding.

Covalently binding sensor coatings is relatively tedious and costly, raising the cost of individual sensors and discouraging end users from reusing sensors. After a prepared crystalline surface is used for measurement, many of its ligand-binding sites are occupied by ligands. Accordingly, the sensor is not suitable for use in measuring the quantity of the same ligand in a different sample solution. In practice, a new sensor is required for each "run", whether the run is for calibration or measurement. Differences between a sensor used in a calibration measurement and one used in a sample measurement result in systematic errors, which impair accuracy.

The need to use different sensors for calibration measurements and sample measurements can be avoided by effective renewal of a sensor. Theoretically, a sensor can be renewed by removing the binder and ligand, then reapplying a binder coating. In practice, it is difficult to remove a covalently bound binder. In addition, covalently re-attaching binder coatings is a critical and expensive operation. Once again, systematic errors loom, since the second coating can differ significantly from the first. It is not feasible for the end user to reapply a covalent binder coating between a calibration run and a measurement. Thus, accuracy is limited where replacement of sensor coatings is required.

Preferably, renewal would be effected by removing ligand without disturbing the binder coating. In this case, the same substrate and coating would be used in both a calibration run and a measurement, minimizing systematic errors. A dissociating treatment can be applied to split specific ligand-to-binder bonds. Care must be taken to remove virtually all the ligand to avoid biasing the succeeding run. However, too strong an application of a dissociation reagent can degrade the binder and even separate it from the crystalline surface.

In theory, the amount of dissociation reagent could be predetermined for each ligand. However, the repeatability of dissociation reagents is imperfect. Variations in ligand conjugates, dissociation reagent concentrations, flow configurations, ambient conditions, and other chemicals in solution can lead to under or over dissociation.

Renewal of sensors with adsorbed binder is less of a problem. While it is difficult to remove attached ligand from the binder without impairing the latter, it is practical to remove the binder along with any attached ligand and then adsorb fresh binder. The problem remains that the new coating can differ randomly from the original.

What is needed is a more accurate mass biosensor method. Such a method should minimize systematic distortions between calibration runs and sample analyses. Moreover, such method should provide for sensor coatings with the stability and predictable orientation characterizing sensors with covalently bound coatings.

SUMMARY OF THE INVENTION

In accordance with the present invention, a mass biosensor method permits monitoring of the dissociation of ligand from binder after measurement is completed. Monitoring dissociation ensures precise renewal of the sensor surface. In other words, sufficient ligand can be removed to allow a sensor to be reused, while excessive dissociations that could impair the binder coating can be avoided.

In the inventive method, the ligand is derivatized with a chelate prior to being specifically bound to the surface of a sensor with a covalently bound binder. After mass measurement, phosphorescence of the ligand chelate can be monitored to determine precisely when the surface is sufficiently free of ligand for a subsequent measurement.

The present invention is compatible with both direct and indirect measurement strategies. In a "direct" realization of the present invention, the analyte in the sample is derivatized with chelate. The resulting analyte chelate is then bound to the sensor. Mass measurement of the analyte chelate is used to calculate the sample analyte concentration. Of course, the added mass due to derivatization with chelate must be taken into account in calculating analyte concentration. In the indirect approach, the complement is derivatized with chelate to form a complement chelate. Once again, the added mass due to derivatization must be accounted for in calculating analyte concentration. In either case, dissociation of the (analyte or complement) ligand chelate can be monitored using phosphorescence measurement.

Depending on the sample, the direct realization of the present invention can encounter problems since derivatization occurs in the sample. The derivatization reaction can be affected by non-analyte sample components, some of which react with the chelate so as to distort the subsequent mass measurement. The indirect realization of the present invention minimizes this problem by providing for derivatizing the complement separately from the sample. Moreover, where derivatization occurs outside the sample, one derivatization can supply ligand chelate for multiple samples.

However, there are times that the chemistry of the direct approach is more accessible than the chemistry of the indirect approach. For example, the procedures for covalently binding antibodies to sensors tend to be better specified than procedures for covalently binding antigens to sensors. The direct approach can take advantage of a better specified binding procedure for an antibody when quantifying an antigen analyte.

The present invention provides for a direct/indirect hybrid approach that is compatible with the chemistry of the direct approach while permitting derivatization outside of the sample, as in the indirect approach. As in the direct approach, the sensor is coated with the complement of the analyte. The analog is derivatized with chelate, rather than the complement as in the indirect approach. A known quantity of analog chelate is added to the sample.

Whereas analyte is specifically bound to the binder in the direct approach, and complement is specifically bound to the binder in the indirect approach, both analyte and analog chelate are bound in the hybrid approach. The analyte and the analog chelate are both ligands and compete for binder complement binding sites in proportion to their concentrations in the sample solution. As in the direct approach, a greater concentration of analyte results in a greater mass measurement. However, in calculating the concentration of the analyte, the known quantity and molecular mass of the analog chelate must be taken into account. The three approaches are contrasted in the table below, with examples in parenthesis given for an antigen analyte.

TABLE I

| Comparison of Biosensor Approaches | | | |
|---|---|---|---|
| | Direct | Indirect | Hybrid |
| Sensor Coating =Binder | complement (antibody) | analog (antigen) | complement (antibody) |
| Ligand | analyte chelate (antigen chelate) | complement chelate (antibody chelate) | analog chelate (antigen chelate) & analyte (antigen analyte) |
| Derivatization | in sample | out of sample | out of sample |
| Analyte | derivative of analyte is the ligand | competes with sensor coating for ligand | competes for binder sites |

In all three strategies, a ligand is chelated to form a phosphorescent complex. Where the ligand provides multiple chelation sites, chelating is maintained below saturation to optimize binding activity of the ligand. Preferably, derivatization leaves sufficient sites so that the ligand retains at least 50% of its binding activity. The metal ion characterizing the (preferably unsaturated) chelate is a lanthanide series element such as europium or terbium. In the direct approach, a chelating agent is added to the sample solution. In the indirect and competitive approaches, the chelating agent can be added to a separate ligand solution. A known quantity of the resulting chelate complex is then added to the sample containing the analyte.

Sample, including the chelated ligand, is introduced to the sample and reference sensors. Both sensors include biochemical layers covalently bound to an underlying sensor substrate, for example, by using an intermediate organosilane coating. The sample sensor coating is the binder, while the reference sensor coating is matched with the binder, but lacks its specific affinity for the ligand. In the direct and indirect approaches, the ligand is the only ligand of interest binding with the binder, whereas in the hybrid approach, the ligand chelate competes with a nonderivatized analyte ligand.

Once the sensor measurements are completed, the sample solution can be washed away. A suitable dissociation reagent is added to dissociate the specific bonds between the binder and the ligand. The concentration of dissociation reagent and the treatment time are preferably limited to minimize damage to the surface, e.g., modification of binder properties and dissociation of the binder from the organosilane coating.

At this stage, the sensor surface is illuminated. The frequency of illumination is selected to stimulate phosphorescence of the chelated ligand. The illumination is removed. Preferably, sufficient time passes to permit intrinsic protein fluorescence to expire before detecting phosphorescence to enhance signal-to-noise ratios.

The phosphorescence is then detected. Phosphorescence can be integrated over a predetermined period, again to improve the signal-to-noise ratio. In the simplest application, the detected phosphorescence can be compared with a threshold to determine whether further renewal is required. If excess phosphorescence is detected, dissociation reagent can be applied again, and the phosphorescence detection steps can be iterated until phosphorescence falls below the threshold. At that point, the method can be reiterated from the beginning. One chelate solution can serve multiple samples in the indirect and competitive approaches. In these cases, reiteration begins with the exposing step, which implicitly involves adding the chelate to the sample solution.

The main objective of the present invention is improved accuracy. Since it is compatible with sensors with covalently bound binder coatings, the present invention provides the advantages of greater stability, and reliably oriented binding sites. Since the invention further allows such sensors to be used with their coatings intact, it provides that the same sensor with the same coating can be used for both calibration runs and the actual sample measurement. Thus, the present invention provides for the use of a reference sample with a ligand chelate, exposing the sample sensor with this ligand chelate, obtaining one or more calibration points, renewing the sensor, and then analyzing a sample. This minimizes systematic errors due to sensor variations between calibration and measurement, enhancing accuracy. Likewise, greater confidence can be placed on comparisons between samples when the same sensor with the same coating is used for different samples.

A serendipitous byproduct of the present invention is the ability to use a sensor many times, instead of only once. More than one hundred uses per sensor is attainable in some cases. This greatly reduces the cost per analysis, and increases the rate at which a series of analyses can be performed. Moreover, the dissociation treatment can be performed with the sensor installed, obviating the time and effort that would be required to remove and reinstall the sensor when the same analyte is to be quantified for successive samples.

The present invention has applications other than monitoring sensor renewal. For example, it can be used in research to assess the effect of a dissociation reagent on a spent sensor. In this case, phosphorescence can be measured to determine the amount of dissociation that occurs. Optionally, phosphorescence can be measured both before and after the treatment is applied. This would entail illuminating the surface twice, once before each phosphorescence measurement. Thus, the present invention can be used to compare dissociation reagents and determine recommended conditions for their application. The results of this research would then permit more informed recommendations to end users involved in sensor renewal.

Thus, the present invention provides for the identification of better dissociation reagents and optimal dissociation conditions. The indirect and hybrid realizations of the present invention avoid problems that might be associated affects of, or difficulties in, derivatizing analyte. The use of phosphorescence to determine the level of dissociation avoids interference by stray fluorescence or by reflected illumination. This latter avoidance is important in connection with sensors using silicon substrates, which have reflective surfaces. Another advantage of the phosphorescence measurements over fluorescence measurement is that phosphorescence of a lanthanide ion protein complex is not quenched by antigen (or antibody) binding. These and other features and advantages of the present invention are apparent from the description below with reference to the following drawings.

DESCRIPTION OF THE PREFERRED EMBODIMENTS

Figure 1:
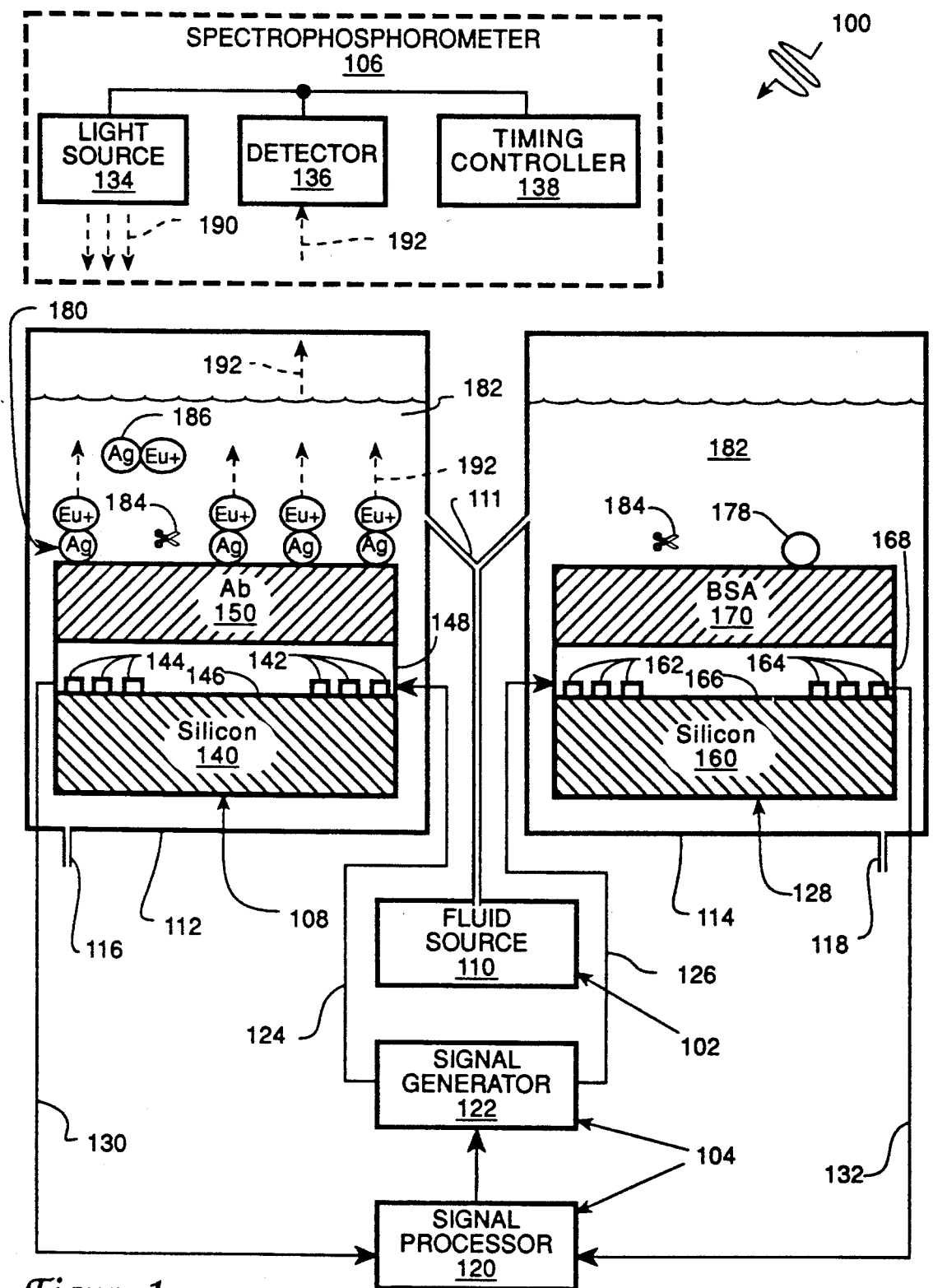
FIG. 1 is a schematic of a mass biosensor system in accordance with the present invention.

The present invention is practiced in the context of a mass biosensor system 100, which comprises a fluid flow subsystem 102, a signal processing subsystem 104, and a spectrophosphorometer 106, as shown in FIG. 1. One application of system 100 is to measure the concentration of an analyte antigen (Ag) in a sample. In a direct realization of the invention, this analyte is derivatized to form an antigen chelate. The rate at which this antigen chelate binds to a sample sensor 108 is used to calculate the original concentration of the antigen in the sample in accordance with algorithms known in the art.

Fluid flow subsystem 102 includes a fluid source 110, which can be used to usher sample, buffer, and a dissociation reagent through a "Y" connector 111, one branch of which leads to a sample chamber 112, and the other of which leads to a reference chamber 114. Fluid exits sample chamber 112 through a fluid exit 116, and exits reference chamber 114 through a fluid exit 118. Signal processing subsystem 104 includes a signal processor 120, a signal generator 122, a sample signal input path 124, a reference signal input path 126, sample sensor 108, a reference sensor 128, a sample signal return path 130, and a reference signal return path 132. Sensors 108 and 128 are located within respective chambers 112 and 114. Spectrophosphorometer 106 includes an illumination source 134, a detector 136, and a timing controller 138.

Sample sensor 108 includes a crystalline silicon substrate 140. Interdigitated input transducers 142 and output transducers 144 are formed on substrate 140. A 500 Å deposition of silicon dioxide 146 covers substrate 140 and transducers 142 and 144 to facilitate adhesion of an organosilane coupling layer 148. Coupling layer 148 provides bonding sites for attachment of an antibody layer 150. The antibody (Ab) is selected to complement the antigen to be assayed. Antibody layer 150 can be replaced by other proteins as appropriate for the particular application system 100.

Reference sensor 128 is nominally identical to sample sensor 108, except the reference coating does not have a specific binding affinity for the analyte. Reference sensor 128 includes a crystalline silicon substrate 160, input transducers 162, output transducers 164, a silicon dioxide layer 166, and an organosilane coupling layer 168. Instead of an antibody layer, reference sensor 128 includes a coating 170 of bovine serum albumin (BSA), which serves as a general purpose reference coating with minimal specific affinity for most antigens.

At the onset of the measurement process, signal processor 120 activates signal generator 122, which then generates a periodic electric signal. This electric signal is divided into a sample signal along line 124 that is directed to sample sensor 108 and a reference signal along line 126 that is directed to reference sensor 128. Input transducers 142 convert the electric sample signal to sample sensor 108 to a periodic acoustic sample signal that is propagated along the surface of substrate 140 to output transducers 144. Output transducers 144 convert the received acoustic sample signal into an electrical output sample signal along line 130. The reference signal through reference sensor 128 undergoes comparable transformations, resulting in an electrical output sample signal along line 132.

Signal processor 120 continuously compares the phases of the sample and reference signals. These signals would be in phase initially, but path length differences typically introduce an initial offset. As analyte antigen (Ag) begins to bind to sample sensor 108, signal processor 120 detects a phase change reflecting a change in propagation velocity of the acoustic signal through sample sensor 108. Changes in the propagation velocity of the acoustic signal through reference sensor 128 reflect factors other than ligand binding. By monitoring the difference in the reference and sample phase changes, that component of the phase change through the sample due to ligand binding alone can be determined.

The initial rate at which ligand binds to the sensor is directly proportional to the concentration of the ligand in the sample. Measurement proceeds until sufficient data has been collected to characterize the slope with confidence, e.g., for three minutes, or until the phase change function loses its linearity. The phase change rate decreases as binder sites are occupied and falls asymptotically to zero as equilibrium is approached.

The measured initial phase change rate is compared to initial phase rates obtained during calibration runs using known concentrations of analyte. The analyte concentration in the sample can be interpolated from multiple calibration points, or extrapolated from a calibration value using a predetermined affinity binding constant associated with the antigen analyte and the antibody binder.

In accordance with the present invention, the analyte antigen is derivatized with a chelating reagent to form an antigen chelate 180, which includes appropriate conjugations of the analyte antigen and a chelating reagent entraining an europium ion ($Eu^{+3}$). Alternatively, another lanthanide metal ion, such as terbium can be incorporated into the chelate complex. In general, one antigen molecule can be derivatized with multiple chelating reagent molecules. However, if every site available on an antigen molecule is occupied by chelating reagent, the antigen activity that promotes binding to the binder can be impaired. Therefore, chelation is implemented so that the antigen complexes are not saturated. Chelating is sufficiently below saturation to permit the antigen activity to remain reasonably high, preferably at least 50%, to promote binding with antibody layer 150.

Once mass measurement is completed for the sample, sensor 108 is not suited for further mass measurements since many of its bonding sites are occupied. Accordingly, the sample can be removed and the sensor exposed to a solution 182 containing a dissociation reagent 184. Hydrochloric acid is a suitable dissociation reagent. Alternatives include, perchlorate, iodide, thiocyanate, urea, and many other reagents.

Ideally, the dissociation treatment would be selected to remove all of the antigen chelate without damaging or removing any molecules of antibody layer 150. Due to their inherent variability, it is preferable to apply a dissociation treatment which is slightly weaker than the ideal. This provides a tolerance that protects the antibody layer in case more disruptive action occurs than planned. Dissociation solution 182 is then washed away, along with any dissociated antigen chelate 186.

At this point, spectrophosphorometer 106 is used to determine the effectiveness of the dissociation treatment. Timing controller 138 causes light source 134 to illuminate (arrows 190) sensor 108 to fully excite the phosphorescence of any remaining antigen chelate 180. The wavelength of illumination is 294 nanometers (nm). Once sufficient time is passed, timing controller 138 turns light source 134 off. Spectrophosphorometer 106 is made by modifying a commercially available spectrofluorometer so that its timing controller performs as described above.

Any antigen chelate still bound to sensor 108 phosphoresces (arrows 192) in a predetermined decay pattern. This phosphorescence is detected by detector 136. The phosphorescence, which, for europium, has a peak at 615 nm, is integrated over a predetermined detection interval. The onset of this detection interval is delayed sufficiently with respect to termination of illumination to permit any protein fluorescence to decay to insignificance before detection begins. The duration of the detection is sufficiently long to ensure detection of phosphorescence in excess of a predetermined acceptability threshold.

The integrated amount is a measure of the amount of antigen chelate bound to sensor 108. If this amount is in excess of the acceptability threshold required for a subsequent use of sensor 108, the dissociation treatment is repeated and the results are once again determined by spectrophosphorometer 106. When phosphorescence is acceptably low, sensor 108 can be used to assay the same analyte in a new sample.

Note that dissociation reagent 184 is conveniently introduced through fluid subsystem 102, so that reference sensor 128 is renewed along with sample sensor 108. Thus, any sample components 178 bound to BSA layer 170 will be dissociated during the renewal process.

Figure 2:
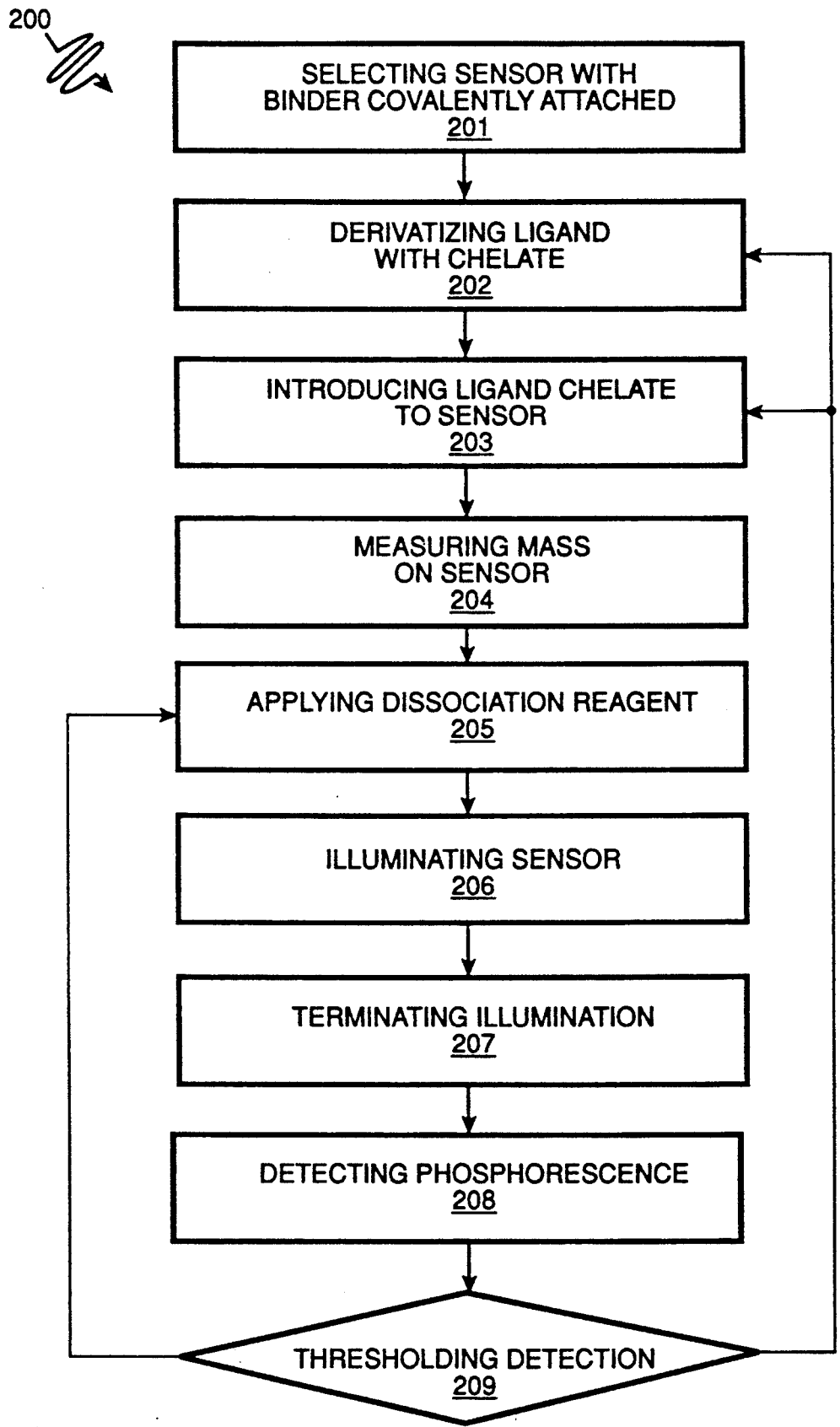
FIG. 2 is a flow chart of the method practiced using the mass biosensor system of FIG. 1.

The foregoing procedure can be recast in more general terms as a method 200, illustrated in the flow chart of FIG. 2. The first step 201 in method 200 is to select an appropriate sample sensor. In practice, the mass biosensor system provides for interchangeable sensors, so that this selection also involves installing sample and reference sensors with a suitable binder coating. An appropriate binder is one that can bind specifically with the ligand. The binder is covalently attached to an aminosilane layer of the sensor.

Another preparatory step involves derivatizing (step 202) the ligand with chelate. Since, in the direct approach, the ligand is the analyte, chelate reagent must be added to the sample and derivatization takes place in the sample. In practice, the ligand is derivatized with a chelating reagent. A source of lanthanide ions, e.g., europium ions, is then added to the sample and a subsequent reaction results in the incorporation of lanthanide ions.

In the indirect and hybrid approaches, the ligand is not the analyte, and therefore derivatization can occur separately from the sample. Where the derivatization occurs separately from the sample, the ligand chelate must be added to the sample solution. Steps 201 and 202 are not temporally ordered; that is, they can occur in either order or concurrently.

The sample with ligand chelate is then introduced (step 203) in the presence of the sample and reference sensors. Mass measurement (step 204) determines the initial phase change rate. As indicated above, this initial phase change rate can be compared to calibration points to calculate the analyte concentration.

Once measurement of the sample solution is completed, renewal of the sensor can begin. The first renewal step (step 205) is applying a dissociation agent for breaking the electrostatic, hydrogen, and van der Waals bonds between the ligand chelate and the binder. Typical substeps include: washing sample from the sample and reference sensors, and bathing the sensors in dissociation agent. The strength of the dissociation agent and the duration the sensor are exposed to it are limited to provide the tolerance required to avoid damage to the binder and reference sensor coatings.

While the dissociation agent is chosen to selectively dissociate the bonds attaching the ligand chelate to the binder, inevitably there is some tendency to structurally alter the binder or its covalent bond to the substrate below. The present invention allows the user to err on the side of too little dissociation to preserve the sensitivity of the sensor. Exposure to the dissociation agent can be terminated by removing the dissociation solution from the sensor and washing the sensor with a suitable buffer.

The next task is to determine the effectiveness of the dissociation treatment. The sensor is illuminated (step 206) with light capable of activating phosphorescence in the bound ligand chelate. Illumination is continued to excite the ligand chelate to saturation. At this point illumination can be terminated (step 207).

Phosphorescence detection (step 208) follows termination of illumination by an interval sufficient to allow protein fluorescence to decay. The sensor substrate is typically of crystalline silicon which is reflective. If the light source remained illuminated, reflections of its output could interfere with detection of chelate emission. In practice, the detector can be on during illumination. In this case, the detector output is sampled during the interval of interest. To enhance the signal to noise ratio, the detector output can be integrated over an interval, taking into account the phosphorescence decay curve in using the integrated amount to indicate the amount of ligand chelate still bound to the sensor.

The detected amount is compared (step 209) to a threshold, either automatically or by an operator. If the detected amount exceeds the threshold, another dissociation treatment is indicated. This can involve repeating steps 205-209. In addition, the difference between the measured amount and the threshold can be used to adjust the dissociation concentration, treatment time, and conditions.

Once the detected amount falls to or below the threshold, the sensor is ready for another analysis. This can obviate the step of selecting a sensor for the next analysis, so the first step for the next iteration can involve derivatizing (step 202) the ligand. However, where the ligand was derivatized separately from the sample, as in the indirect and hybrid approaches, this step can be skipped if there is sufficient ligand chelate available from the previous analysis. Thus, the next analysis can begin with either step 202 or step 203. This renewal method can, in some cases, allow in excess of one hundred uses of a sensor before the dissociation treatments cause the sensor to deteriorate below a useful level of performance.

Figure 3:
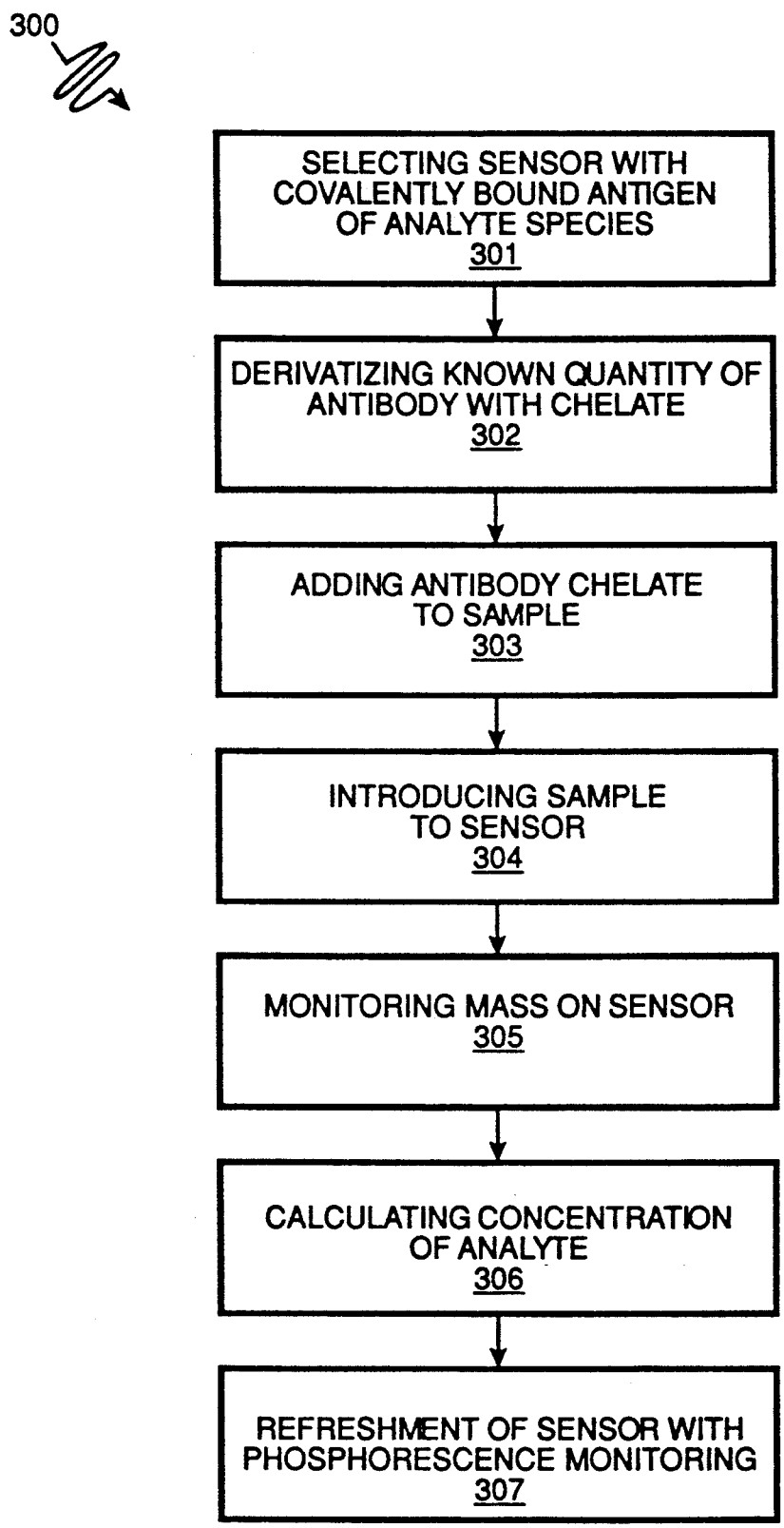
FIG. 3 is a flow chart of an indirect approach to quantification of an antigen in accordance with the present invention.

An indirect method 300 in accordance with the invention is shown in the flow chart of FIG. 3. This method is indirect in that the analyte is not bound to the sensor; its concentration is determined indirectly by monitoring the binding of another entity (the complement). In the case of an antigen analyte, it is the antibody complement that is bound and measured. Since the antibody is the ligand, the binder is selected (step 301) to be the analyte of interest, or another analog thereof.

The common antibody for the analog binder and the sample analyte is derivatized (step 302) with a chelating reagent. Derivatization can be performed apart from the sample solution so that the reactions involved do not affect sample components. The antibody chelate is added (step 303) to the sample. The augmented sample is introduced (step 304) to the sample sensor.

As the augmented sample flows over the sample sensor, the surface-bound binder analog and the sample analyte compete for the antibody chelate. Since the amount of antibody chelate introduced into the sample is known, the phase change rate that would occur in the absence of any sample analyte is determined. The actual phase change rate is less than this reference to the extent that sample analyte is present in the sample, competing with the bound analog. Thus, measuring (step 305) the initial phase rate change permits the analyte concentration in the sample to be calculated (step 306).

Calculation step 306 can be implemented immediately, or postponed until after other steps are completed. Additional measurements can be taken to monitor antibody behavior. Renewal (step 307) proceeds in accordance with steps 205-209 of method 200.

Figure 4:
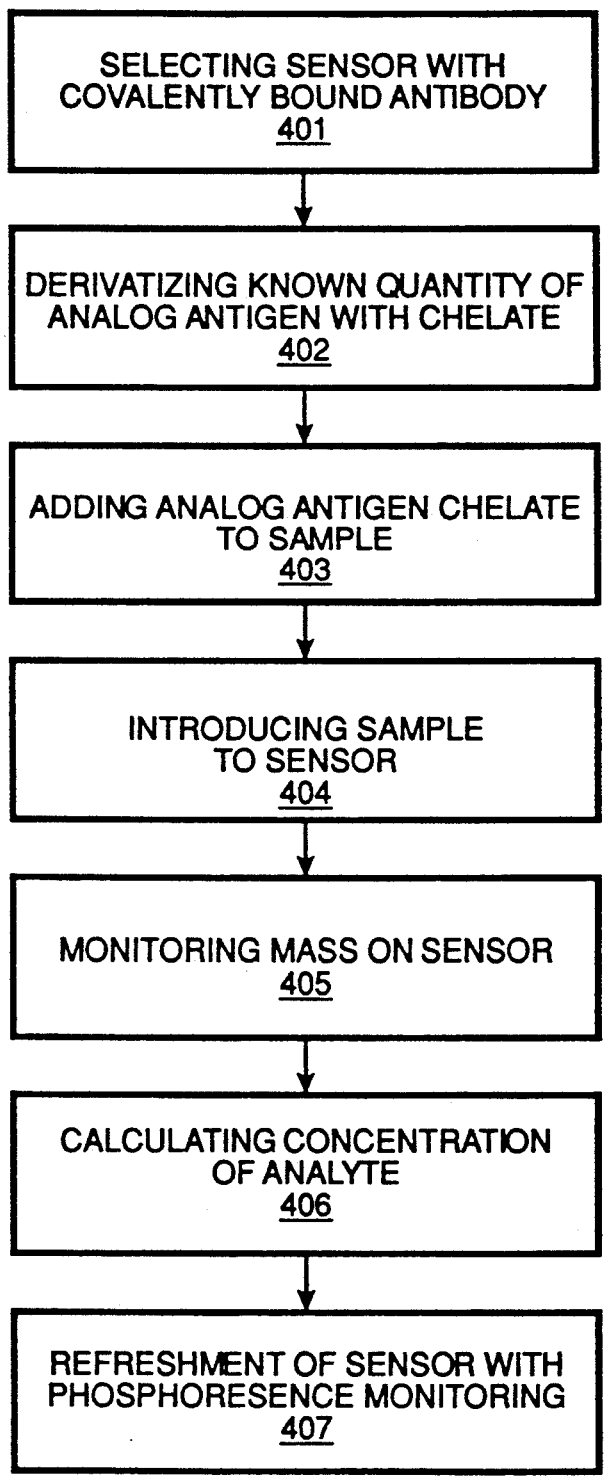
FIG. 4 is a flow chart of a hybrid approach to quantification of an antigen in accordance with the present invention.

A hybrid method 400 of the present invention is shown in the flow chart of FIG. 4. Hybrid method 400 is similar to the direct method in that analyte is bound to the sensor; hybrid method 400 is similar to the indirect method in that a non-analyte is derivatized with chelate outside the sample and bound to the sensor. The hybrid analysis differs from the indirect analysis in that analyte is bound as ligand to the sensor, but also differs from the direct analysis in that the analyte is not derivatized and in that analog ligand chelate is also attached along with sample analyte.

As in the direct approach, the sensor is selected (step 401) so that the binder is the complement for a selected analyte. Thus, for an antigen analyte, the binder can be the corresponding antibody. Analyte not in the sample, or an another analog of the analyte, is derivatized (step 402) with chelate to form an analog chelate, which in this case is an antigen chelate. A known amount of this antigen chelate is added (step 403) to the sample.

The augmented solution is introduced (step 404) to the sensors. The analyte and the analog chelate compete for sites on the binder antibody. A mass measurement is obtained (at step 405) in the form of the initial phase change rate. The combined concentration of antigen and chelated complex can then be calculated from the affinity binding constants of the analyte and the analog. The analyte concentration can then be calculated (step 406) since the total amount of analog chelate is given. Renewal (step 407) proceeds in accordance with steps 205-209 of method 200.

The hybrid approach shares advantages of both the direct and the indirect approaches. Like the direct approach, the competitive approach takes advantages of the generally greater availability of immobilization schemes for attaching antibodies to surfaces. Like the indirect approach, the competitive approach permits derivatization to be performed outside the sample. This external derivatization permits one derivatization to be applied to several sample measurements, and minimizes undesired effects of the derivatization reaction on other sample components. On the other hand, the indirect approach can achieve greater analyte sensitivity, since ligand chelate does not have to compete for surface sites in the indirect approach.

Figure 5:
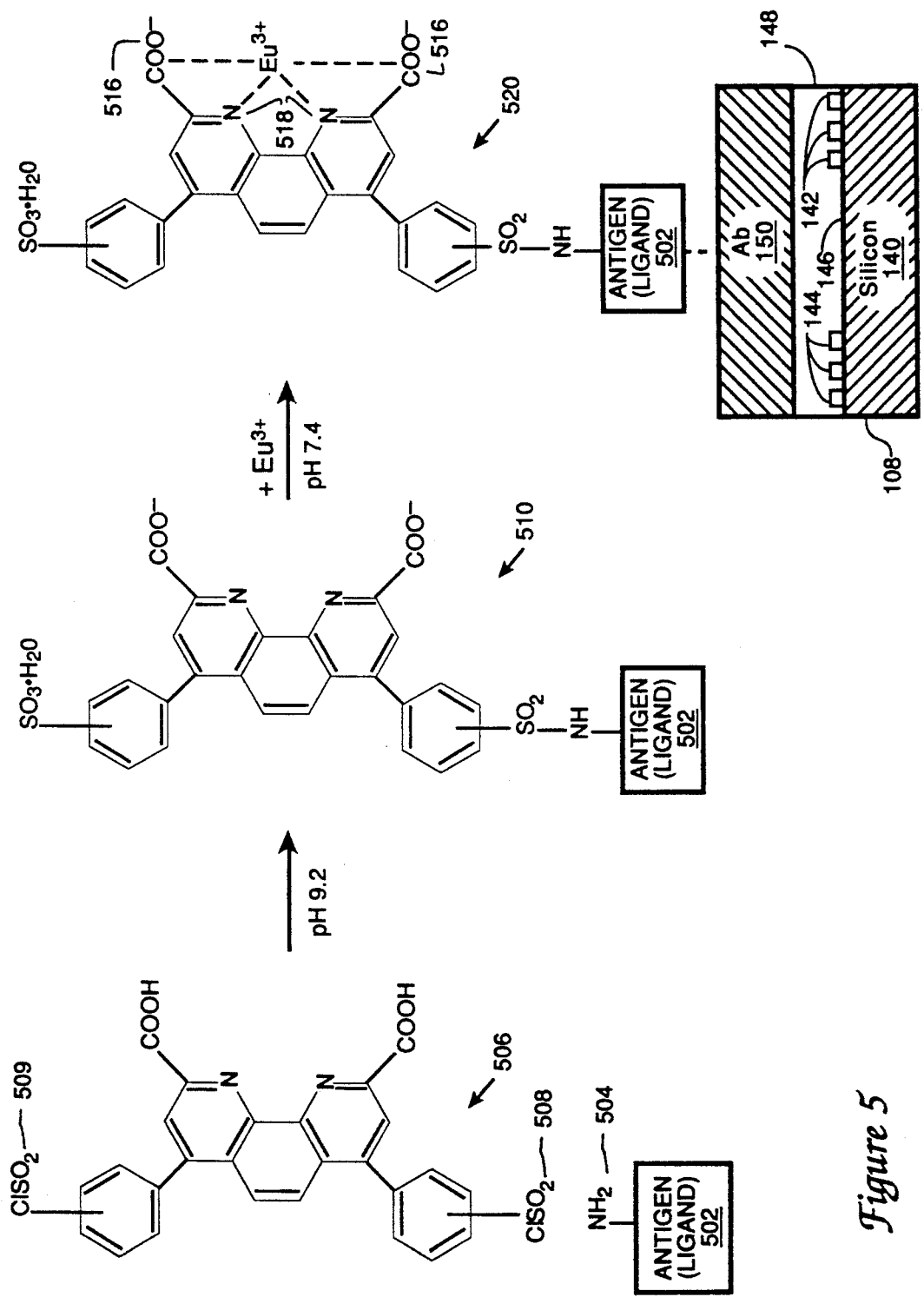
FIG. 5 is a schematic illustration of a derivatization of an antigen to form a chelate as provided for by the present invention.

The process for derivatizing a ligand 502 is illustrated in FIG. 5. Ligand 502 can be an antibody, an antigen, another protein or any molecule which contains primary amine functional groups. Primary amine ($-NH_2$) groups 504 are available on a protein at lysine and arginine residues and at peptide amine termini. Ligand 502 is derivatized with 4,7-bis(chlorosulfophenyl)-1,10-phenanthroline-2,9-dicarboxylic acid (BCPDA 506), the derivative serving as a lanthanide chelating agent 510. The amount of BCPDA 506 added is less than that required to bind all the free amine groups 504 of ligand 502, so that the resulting reagent complex is unsaturated, and so that at least 50% of the binding activity of ligand 502 is preserved.

In this derivatization, a primary amine group 504 of ligand 502 binds with a chlorosulfonic acid group 508 of BCPDA 506. A second chlorosulfonic acid group 509 is hydrolyzed. Unbound BCPDA is removed by size-exclusion gel chromatography. Excess lanthanide ion $Eu^{3+}$ is added and combines with carboxyl groups 516 and phenanthroline nitrogens 518 of chelating agent 510, to form ligand chelate 520. This formation then attaches to the sample sensor. The chemistry for this derivatization is adapted from Ramon A. Evangelista et al., "A New Europium Chelate for Protein Labelling and Time-Resolved Fluorometric Applications", *Clinical Biochemistry*, Vol. 21, June 1988, pp. 173–178.

Figure 6:
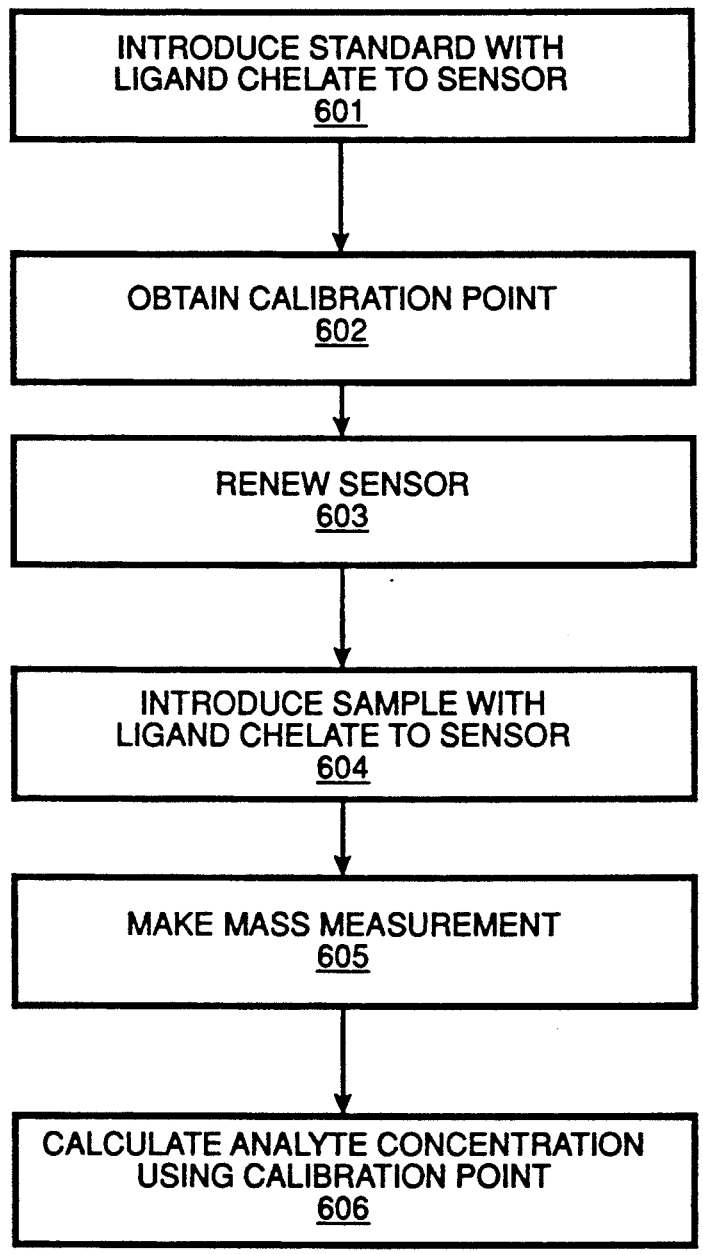
FIG. 6 is a flow chart of the present invention as applied to sensor calibration and analyte quantification.

The application of the present invention to calibration is depicted in a method 600, flow charted in FIG. 6. A reference solution is prepared with a known quantity of the analyte of interest. The reference solution includes a known quantity of ligand chelate, which can be a derivatized form of the analyte, its complement, or its analog, depending on analysis strategy. This reference solution is introduced (at step 601) to the sample and reference sensors, prepared in accordance with the selected strategy. The initial rate of phase change is noted. A calibration point is obtained (at step 602) by associating this initial rate of phase change with the known analyte quantity and known ligand chelate quantity. (In the direct strategy, these quantities are one and the same.) Additional calibration points can be obtained in the same manner. The sensor is renewed (at step 603) as described with reference to steps 205–209 in FIG. 2.

These preliminaries are followed by the steps of any of the methods 200, 300, and 400. Summarizing, a sample bearing a ligand chelate is introduced (at step 604) to the renewed sample sensor, a mass measurement is made (at step 605), and the analyte concentration is calculated (at step 606) from the mass measurement and the calibration point or points.

In the examples below, Example 1 pertains to all three methods, direct, indirect, and hybrid. Examples 2–7 apply the direct and hybrid methods. Examples 8 and 9 provide the necessary additional information required for practicing the indirect method.

EXAMPLE 1

Binding Aminosilane to Silicon Substrate

Crystalline silicon substrate was coated with 500 Å silica ($SiO_2$). One milliliter (mL) aminopropyltriethoxy silane was diluted with 24 mL 95% alcohol. The solution pH was adjusted to 4.5 with 6N HCl and allowed to hydrolyze for 5–10 minutes. The silica surface was coated with the dilute silane and the reaction continued for one hour at room temperature. The silica surface was covered to prevent evaporation of the reagents during incubation. The silica surface was rinsed three times with 95% alcohol and then dried at 110° for 10 minutes.

EXAMPLE 2

Covalently Binding Antibody to Sensor 250 mL of 1 mg/mL G-anti-Human (GaH) IgG was diluted 1:10 in 0.1 molar (M) sodium phosphate, pH 6.0 containing 10 mM $NaIO_4$ (0.11 g/50 mL). The oxidation reaction was allowed to proceed for 30 minutes at 4° C., at which time the $NaIO_4$ was removed via a 10 mL gel filtration chromatography column that had been pre-equilibrated with 0.1M sodium phosphate, pH 7.4. The eluted, oxidized GaHIgG was incubated with the organosilane surface for 2 hours at 4° C. with gentle agitation. This incubation created a Schiff base imine, serving to covalently bind the antibody to the organosilane. The Schiff base imine was stabilized with 0.01M $NaCNBH_4$ by adding 100 µL of 0.1M $NaCNBH_4$ (0.06 g/10 mL sodium phosphate, pH 6.0), to each 1 mL of oxidized antibody. The surface was then incubated for several hours (overnight) with gentle agitation at 4° C., and rinsed three times with 0.1M sodium phosphate, pH 7.4 and aspirated dry. The antibody-derivatized surface was stored desiccated at 4° C. for subsequent use.

EXAMPLE 3

Conjugation of HIgG antigen with BCPDA

Human immunoglobulin G (HIgG), 150 microliter (µL) of 18.6 milligrams per milliliter (mg/mL), was centrifuged and diluted into 7.5 mL of 100 millimolar (mM) $NH_4HCO_3$, pH 9.2. This solution was then divided into three 6.2 nanomolar (nM) aliquots of 2.5 mL each, further denoted A, B, and C.

A 9.5 mM stock solution of BCPDA (synthesized as described in Ramon A. Evangelista et al., "A New Europium Chelate for Protein Labelling and Time-Resolved Fluorometric Applications", *Clinical Biochemistry*, Vol. 21, June 1988, pp. 173–178) was prepared by dissolving 5.9 mg of said reagent in 1 mL absolute ethanol. 200 µL of this solution was added to 400 µL absolute ethanol to generate a 3.2 mM BCPDA solution. To A was added 98 µL of the 9.5 mM BCPDA solution (150×molar excess) in four 24.5 µL increments over a period of 2 minutes. Likewise, to each of B and C was added 98 µL of the 3.2 mM BCPDA solution (50×molar excess). This resulted in protein chelate reagent solutions A, B, and C.

Protein chelate reagent solutions A and B were gently agitated for 30 minutes at room temperature. C was allowed to react for only 5 minutes. Three 10 mL gel filtration chromatography columns, pre-equilibrated with 50 mM tris(hydroxymethyl)aminomethane, or "tris", pH 7.4, were used to separate the chelate derivatized protein from the free chelate. The eluents were additionally microdialyzed, using a microdialyzer handling 250 µL per well, for 2 hours at room temperature to ensure the removal of unbound BCPDA.

EXAMPLE 4

Formation of HIgG-BCPDA-$Eu^{+3}$

To 3 mL of 10 microgram per milliliter (µg/mL) HIgG-BCPDA was added 18 µL of 3 mM $EuCl_3$ solution (4 mg $EuCl_3 \cdot 6H_2O$ in 3.3 mL HCl). The complexation was allowed to proceed for 18 hours at 4° C. with gentle agitation.

EXAMPLE 5

Reaction of HIgG-BCPDA-$Eu^{+3}$ with Surface Immobilized GaHIgG.

HIgG-BCPDA-$Eu^{+3}$ (10 µg/mL in 50 mM tris pH 7.4) was diluted 1:1 in the same buffer containing 2% BSA and 0.1% polyoxyethylenesorbitan monolaurate (Tween 20) for a final solution containing 5 µg/mL HIgG in 50 mM tris, pH 7.4/1% BSA/0.05% Tween 20. A silicon substrate (½ cm × 1 cm) containing a 500 Å surface layer of $SiO_2$ which was derivatized with aminopropyltriethoxysilane and GaHIgG antibody was incubated with the HIgG-BCPDA-$Eu^{+3}$ for 2 hours at room temperature with gentle agitation, rinsed twice with high-performance liquid chromatography water containing the same $EuCl_3$ concentration, and then air dried.

EXAMPLE 6

Phosphorescence Measurement of Surface-Bound HIgG-BCPDA-$Eu^{+3}$

A spectrofluorometer (Perkin-Elmer LS-5) equipped with a front surface scattering cell compartment is used for phosphorescence studies. The 1×½ cm silica substrates are mounted in the sample cell. Phosphorescence data are collected under the measurement conditions shown in Table II.

TABLE II

| Phosphorescence Data Collection Conditions | |
|---|---|
| excitation slit width | 10 nm |
| emission slit width | 20 nm |
| scan rate | 60 nm/min |
| delay time | 70 μsec |
| gate time | 1.5 msec |
| excitation wavelength | 294 nm |

EXAMPLE 7

Quantitation of HIgG-BCPDA Activity

The activity of the derivatized HIgG was measured by ELISA methodology. Two standard 96-well flat-bottom polystryrene plates were incubated for 1 hour at 37° C. with 100 μL GaHIgG at eight serial dilution concentrations ranging from 1250 to 1.2 ng/mL (nanograms per milliliter) in phosphate buffered saline. The plates were then washed three times with 50 mM tris buffer, pH 7.4.

The derivatized antigen solutions A, B, and C and a native HIgG control sample were each diluted to 18.6 μg/mL (micrograms per milliliter) in 50 mM tris buffer, pH 7.4/1% BSA/0.05% Tween 20. The diluted antigen solutions were reacted in triplicate with the antibody-coated wells (100 μL/well) for 1 hour at room temperature (RT) with gentle agitation followed by washings, as described above. Each well was then blocked with 200 μL of a 2% BSA solution (0.5 g BSA in 50 mM tris, pH 7.4) for 20 minutes at RT and then washed three times with phosphate buffered saline (PBS).

The secondary antibody, GaHIgG-peroxidase at 1 mg/mL, was diluted 1:400 in PBS containing 1% BSA and 0.05% Tween 20 (45 μL antibody/18 mL buffer). Each well was incubated with 100 μL of this solution for 2 hours at RT with gentle agitation, followed by three washes with phosphate buffered saline. 150 mg o-phenylenediamine were dissolved in 36 mL 0.1M citrate, pH 5.0, followed by the addition of 360 μL 3% peroxide. Each well was then incubated with 100 μL of this mixture for five minutes at RT with gentle agitation followed by quenching with 100 μL 2N sulfuric acid. The plates were then measured, yielding the following relative activities:

TABLE III

| Quantitation of Antibody Activities | | |
|---|---|---|
| HIgG | native | 1.00 |
| A: | 150x; 5 min | 0.3 ± 0.1 |
| B: | 50x, 5 min | 0.70 ± 0.09 |
| C: | 50x, 30 min | 0.63 ± 0.07 |

As sample B appeared to be the most active HIgG, it was used for all subsequent studies.

EXAMPLE 8

Attachment of Human IgG Antigen to Aminosilane Surface 250 mL of 18.6 mg/mL Human IgG was diluted 1:10 in 0.1M sodium phosphate, pH 6.0 containing 10 mM $NaIO_4$ (0.11 g/50 mL). This solution was oxidized in the presence of a silicon dioxide coated substrate coated with aminosilane as in Example 1. The oxidation reaction was allowed to proceed for 30 minutes at 4° C. with gentle agitation, resulting in a Schiff base imine serving to covalently bind to the substrate. The Schiff base imine was stabilized with 0.01M $NaCNBH_4$ by adding 100 μL of 0.1M $NaCNBH_4$ (0.06 g/10 mL sodium phosphate, pH 6.0) to each 1 mL of oxidized antibody. The surface was then incubated overnight with gentle agitation at 4° C., rinsed three times with 0.1M sodium phosphate, pH 7.4 and aspirated dry. The antigen-derivatized surfaced was stored desiccated at 4° C. for subsequent use.

EXAMPLE 9

Conjugation of GaHIgG Antibody with BCPDA

50 μL GaHIgG (1 mg/mL) was centrifuged and diluted to 2.5 mL with 100 mM ammonium carbonate, pH 9.2 in a 3.5 mL polypropylene test tube. A 0.6 mM solution of BCPDA, synthesized as in Example 2, was prepared by dissolving 2.2 mg of said reagent in 600 μL absolute ethanol and then diluting this solution 1:10 in 1 mL absolute ethanol. Four 25 μL increments of the BCPDA reagent were added to the antibody solution over a period of two minutes with gentle mixing between increments. The reaction proceeded for 30 minutes at room temperature, after which a 10 mL gel filtration chromatography column pre-equilibrated with 50 mM tris, pH 7.4, separated the chelated protein and hydrolyzed BCPDA. The eluent can be additionally purified with a microanalyzer to assure complete removal of non-covalently bound chelate reagent.

Preparation of the reference sensor follows example 1 through the attachment of the aminosilane layer. In place of the binder (antibody in example 2 and antigen in example 8), a non-selective coating is applied to the reference sensor. BSA can be used as a general purpose reference sensor coating. Those skilled in the art can adjust the methods of examples 2 and 8 to provide for covalent binding of BSA to the sensor already coated with aminosilane.

In general, it is desirable to coat the reference sensor with material having a molecular mass as close as possible to that of the binder. In some cases, a general purpose reference coating may not provide the desired match of molecular masses. As an alternative to non-selective coatings, a selective coating can be applied to the reference sensor. For example, fibronectin, which has a molecular mass relatively close to that of GaHIgG antibody, can be applied as the reference coating, provided the corresponding antigen is absent from the sample.

The example cited details the measurement of antibody (IgG) proteins since these are commonly used as binding components. However any proteins may be used (e.g. DNA-binding proteins, Protein G, lectins, and enzymes). While quantifying protein is the major objective of the invention, the method can be applied to any molecules having primary amine groups, for example, amino sugars and nucleic acids bound to a surface. Other ligand/binder pairings provided by the present invention are presented in the following table.

TABLE IV

| Binder Coatings and Corresponding Ligands | |
|---|---|
| Antibodies (all classes) | Epitopes |
| polyclonal | idiotypes |
| monoclonal | (paratopes) |
| fragments (Fc, Fab, F(ab)'$_2$) | genetically engineered or synthesized isolates or epitopes |
| recombinant forms of the above | polypeptieds, haptens |

TABLE IV-continued
Binder Coatings and Corresponding Ligands

| | |
|---|---|
| catalytic antibodies | |
| Protein A | immunoglobulins |
| Lectins | glycoproteins |
| | glycosylated-ligands |
| concanavalin A | glucose |
| Lipids | |
| micelle | occluded species |
| liposome | occluded species |
| phospholipid | complementary amphipath |
| Avidin | biotinylated-ligands |
| Streptavidin | |
| DNA | oligonucleotides |
| RNA | DNA strands |
| nucleic acids | fragments (isolate or recombinant) |
| Anti-sense DNA | Messenger RNA |
| Anti-sense RNA | |
| Receptors | |
| neural | cholenergic, adrenergic species |
| enzyme | enzyme |
| cell membrane | cell membrane |
| hormone | hormone |
| viral | virus |
| bacterial | bacteria |
| phallotoxins | actin |
| Enzyme | Cofactor |
| cytochrome | heme |
| ferredoxins | Fe—S clusters |
| metalloenzymes | |
| carboxypeptidase A | —$Zn^{2+}$ |
| siderophores | —$Fe^{2+}$ |
| Chelate Complex | Cation |
| cryptate | many species |
| anionic polymer | many species |
| valinomycin | —$K^+$ |
| vitamin $B_{12}$ | —$Co^{2+}$ |
| fura-2, indo-1, diacylglycerols | —$Ca^{2+}$ |

As indicated by the foregoing table, the present invention has a range of applications. Environmental applications include soil analysis, water analysis, ground water analysis, and analysis of chemical spills. Water analyses can be used, for example, to measure the presence of pesticides, polyaromatic hydrocarbons, and phthalates. Food and feed can be analyzed to determine the quality and exposure to pesticides. Pesticide analyses using the present invention can determine concentrations of triazines, chloro-acetanalides, pyrazoles, and pyrroles, for example. In addition, the present invention provides for a variety of clinical chemistry applications, including diagnostics, therapeutics, and physiological monitoring.

The present invention provides for a variety of techniques for forming a ligand chelate. In the embodiment described above, the ligand was first derivatized with a chelating reagent lacking a metal ion. The metal ion was then added in a following step. Alternatively, the ligand can be derivatized with a chelating reagent already including a metal ion. A ligand molecule is unsaturated with chelate if at least one of its sites available for binding a chelating reagent molecule lacks a chelating reagent molecule or one of the sites occupied by a chelating reagent molecule lacks a metal ion.

The present invention provides for permutations in the order of steps. In the preferred indirect and hybrid approaches, chelation of the ligand occurs prior to the introduction of the ligand to the sample. In the direct approach, chelation occurs in the sample. In the preferred embodiments describe above, chelation occurs before introducing the sample to the sensor. However, it can also occur after sample introduction and measurement. In the latter case, it is feasible to perform at least one dissociation treatment before chelation. In general, it is preferable to chelate before sample introduction to minimize sample run time and enhance measurement throughput: furthermore, chelating after measurements does not allow one derivatization to be applied to multiple samples. On the other hand, and this especially pertains to the direct approach, post-measurement chelation has the advantage of avoiding any distortion that chelation might induce.

The invention accommodates any type of sensor, so that acoustical, optical, gravimetric, electrochemical, photoelectrochemical, capacitance, and thermistor sensors are all within the scope of the invention. Introduction of sample to a sensor can involve flowing sample over a sensor, or inserting a sensor into a volume of sample. The sample can be divided and introduced in parallel to the sample and reference sensors. Alternatively, the sample can be introduced serially to the sensors.

Fiber optic evanescent sensors and evanescent planar waveguide sensors are among the possible optical sensors. For example, an optical fiber can be coated with chelated antigen. The coated fiber can be enclosed in a hydrophilic membrane, and this assembly can be inserted into a sample solution, which can be in vivo. The optical output of the fiber decreases as the antigen in solution replaces bound antigen. This optical intensity decreased can be monitored to determine the original antigen concentration in the sample solution. More generally, phosphorescence measurements can be used to measure competitive displacement of a chelated antigen by a free analyte on a wide variety of surfaces. These and other modifications to and variations upon the described embodiments are provided for by the present invention, the scope of which is limited only the following claims.

What is claimed is:

1. A mass biosensor method for determining the presence of an analyte comprising the steps of:
   selecting a ligand wherein said ligand is said analyte, an analog of said analyte, or a complementary binding partner of said analyte;
   derivatizing said ligand to provide a phosphorescent ligand chelate;
   setting up a sensor having a binder covalently attached thereto, said binder being selected to specifically bind said ligand;
   contacting said sensor with a mixture so that at least some of said ligand binds to said binder, said mixture including at least some ligand chelate, said mixture including at least some analyte;
   monitoring the mass on said sensor by detecting an affect of said mass on said sensor so that the amount of said analyte in said sample can be determined;
   applying a dissociation treatment to said sensor so as to dissociate at least some of said ligand chelate from said binder;
   illuminating said sensor with light capable of exciting said ligand chelate;
   removing the illumination; and
   detecting phosphorescence emitted from said sensor; whereby an indication of nondissociated ligand chelate remaining on said sensor is obtained.

2. A method as recited in claim 1 wherein if the detected phosphorescence is above a predetermined threshold, said method is repeated from said applying step.

3. A method as recited in claim 2 wherein if said detected phosphorescence is below said threshold, said method is repeated either from said derivatizing step or said introducing step.

4. A method as recited in claim 3 further comprising the following calibration steps:
 introducing to a sample sensor a reference solution bearing a known quantity of said analyte and a known quantity of said ligand chelate;
 obtaining a calibration point by measuring mass change at said sample sensor and associating this measurement with said known quantities; and
 renewing said sample sensor by implementing steps substantially identical to those beginning with said step of applying a dissociation treatment.

5. A method as recited in claim 1 wherein said ligand is derivatized with chelate in such a manner that said ligand remains unsaturated with said chelate.

6. A method as recited in claim 5 wherein said ligand remains sufficiently unsaturated to retain at least 50% of its activity.

7. A method as recited in claim 1 wherein said derivatizing step involves derivatizing ligand in said sample before said introducing step.

8. A method as recited in claim 1 further comprising a step of adding said ligand chelate to said sample before said introducing step.

9. An analytical method comprising the steps of:
 selecting a sensor having an analog of an analyte covalently attached thereto;
 selecting a complementary binding partner capable of specifically binding with said analyte and said analog;
 derivatizing with a chelating agent said complementary binding partner to form a complementary binding partner chelate that is phosphorescent;
 adding a known quantity of said complementary binding partner chelate to a sample including said analyte to provide a mixture;
 introducing said mixture to said sensor;
 applying a dissociation treatment to said sensor so as to dissociate at least some complementary binding partner chelate from said analyte analog;
 illuminating said sensor with light capable of exciting phosphorescence in said complementary binding partner chelate;
 terminating the illumination;
 detecting phosphorescence emitted from said sensor; and
 reiterating from said step of applying said dissociation treatment until the detected phosphorescence is acceptably low.

10. A method as recited in claim 9 further comprising the steps of
 measuring the mass of complementary binding partner chelate specifically bound to said analog, said measuring being performed using a mass biosensor system incorporating said sensor, said measuring occurring after the beginning of said introducing step and before said step of applying said dissociation treatment; and
 calculating the concentration of said analyte in said sample.

11. An analytical method comprising the steps of:
 selecting a sensor having a complementary binding partner covalently attached thereto;
 derivatizing with a chelating reagent an analog of an analyte to form an analog chelate, said analog being capable of specifically binding to said complementary binding partner;
 adding a known quantity of said analog chelate to a sample including said analyte to provide a mixture;
 introducing said mixture to said sensor;
 applying a dissociation treatment to said sensor so as to dissociate at least some analog chelate from said complementary binding partner;
 illuminating said sensor with light capable of exciting phosphorescence in said analog chelate;
 terminating the illumination;
 detecting phosphorescence emitted from said sensor; and
 reiterating from said step of applying said dissociation treatment if the detected phosphorescence is unacceptably high.

12. A method as recited in claim 11 further comprising the steps of:
 measuring the total mass of analyte and analog chelate covalently bonded to said sensor via said complementary binding partner, said measuring occurring after the beginning of said introducing step and before said step of applying dissociation treatment to said sensor; and
 calculating the concentration of said analyte in said sample.

* * * * *